(12) United States Patent
Yun

(10) Patent No.: US 8,571,650 B2
(45) Date of Patent: Oct. 29, 2013

(54) METHODS AND COMPOSITIONS FOR TREATING A RENAL ASSOCIATED CONDITION IN A SUBJECT

(75) Inventor: Joonkyoo Anthony Yun, Palo Alto, CA (US)

(73) Assignee: Palo Alto Investors, Palo Alto, CA (US)

(*) Notice: Subject to any disclaimer, the term of this patent is extended or adjusted under 35 U.S.C. 154(b) by 890 days.

(21) Appl. No.: 11/713,555

(22) Filed: Mar. 2, 2007

(65) Prior Publication Data

US 2007/0208382 A1    Sep. 6, 2007

Related U.S. Application Data

(60) Provisional application No. 60/856,106, filed on Nov. 1, 2006, provisional application No. 60/778,870, filed on Mar. 3, 2006.

(51) Int. Cl.
*A61N 1/05*    (2006.01)

(52) U.S. Cl.
USPC .................... 607/2; 607/40; 607/44

(58) Field of Classification Search
USPC .................................. 607/2, 40, 44
See application file for complete search history.

(56) References Cited

U.S. PATENT DOCUMENTS

| | | | |
|---|---|---|---|
| 6,086,527 A | 7/2000 | Talpade | |
| 6,978,174 B2 | 12/2005 | Gelfand et al. | |
| 2001/0053795 A1* | 12/2001 | Bond | 514/551 |
| 2002/0091349 A1* | 7/2002 | Reich | 604/5.01 |
| 2003/0216792 A1 | 11/2003 | Levin et al. | |
| 2004/0249416 A1* | 12/2004 | Yun et al. | 607/2 |
| 2005/0192638 A1 | 9/2005 | Gelfand et al. | |
| 2005/0228459 A1 | 10/2005 | Levin et al. | |
| 2005/0228460 A1 | 10/2005 | Levin et al. | |
| 2005/0234523 A1 | 10/2005 | Levin et al. | |
| 2005/0267010 A1 | 12/2005 | Goodson et al. | |
| 2005/0288730 A1 | 12/2005 | Deem et al. | |
| 2006/0025821 A1 | 2/2006 | Gelfand et al. | |
| 2006/0041277 A1 | 2/2006 | Deem et al. | |
| 2006/0116721 A1 | 6/2006 | Yun et al. | |
| 2006/0235474 A1* | 10/2006 | Demarais | 607/2 |

* cited by examiner

*Primary Examiner* — Joseph Dietrich
(74) *Attorney, Agent, or Firm* — Bret E. Field; Bozicevic, Field & Francis, LLP

(57) ABSTRACT

Methods for treating a renal associated condition in a subject are provided. Aspects of the subject methods include paradoxically enhancing renal sympathetic bias in the subject in a manner effective to treat the renal associated condition. Also provided are compositions, kits and systems for practicing the subject methods.

15 Claims, 1 Drawing Sheet

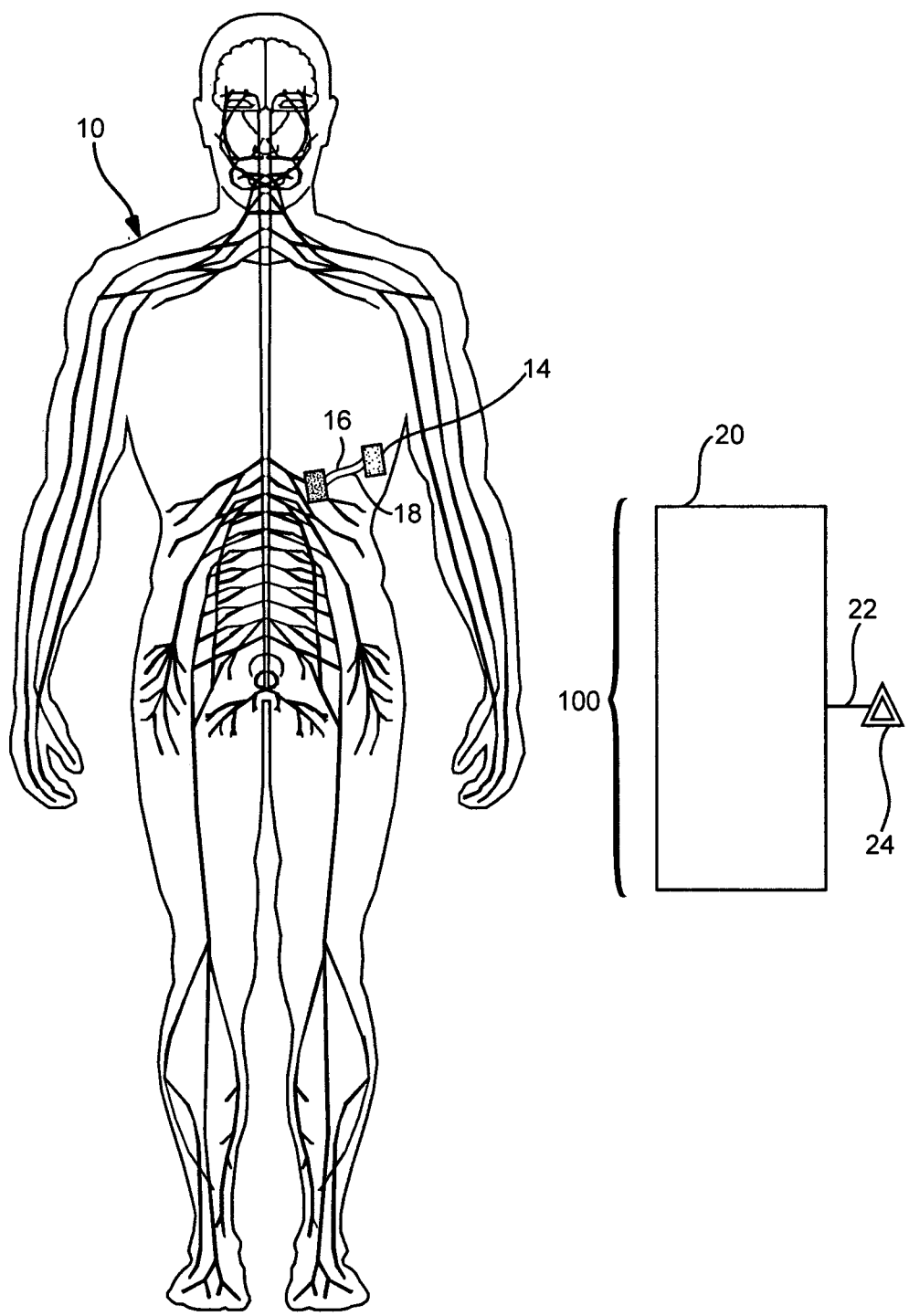

METHODS AND COMPOSITIONS FOR TREATING A RENAL ASSOCIATED CONDITION IN A SUBJECT

CROSS-REFERENCE TO RELATED APPLICATIONS

Pursuant to 35 U.S.C. §119 (e), this application claims priority to the filing date of U.S. Provisional Patent Application Ser. No. 60/856,106 filed Nov. 1, 2006 and to the filing date of U.S. Provisional Application Ser. No. 60/778,870 filed Mar. 3, 2006; the disclosures of which applications are herein incorporated by reference.

BACKGROUND

The kidneys are a pair of organs that lie in the back of the abdomen on each side of the vertebral column. Kidneys play an important regulatory role in maintaining the homeostatic balance of the body. The kidneys function like a complex chemical plant. The kidneys eliminate foreign chemicals from the body, regulate inorganic substances and the extracellular fluid, and function as endocrine glands, secreting hormonal substances like renin and erythropoietin.

The main functions of the kidney are to maintain the water balance of the body and control metabolic homeostasis. Healthy kidneys regulate the amount of fluid in the body by making the urine more or less concentrated, thus either reabsorbing or excreting more fluid, respectively.

In case of renal disease, some normal and important physiological functions become detrimental to the patient's health. This process is called overcompensation. In the case of Chronic Renal Failure (CRF) patients overcompensation often manifests in hypertension (pathologically high blood pressure) that is damaging to heart and blood vessels and can result in a stroke or death.

The functions of the kidney can be summarized under three broad categories: a) filtering blood and excreting waste products generated by the body's metabolism; b) regulating salt, water, electrolyte and acid-base balance; and c) secreting hormones to maintain vital organ blood flow. Without properly functioning kidneys, a patient will suffer water retention, reduced urine flow and an accumulation of wastes toxins in the blood and body.

The kidney is made up of about a million tiny units called nephrons. The nephron is where blood carrying capillaries intertwine with tiny waste-processing tubules. A complicated chemical exchange takes place in the nephron where waste materials and water leave the blood via the capillaries and enter the urinary system via the tubules. Every day a person's kidneys sift out about 2 quarts of waste products and excess water from the blood. On average the kidneys process about 200 quarts of blood. The waste and extra water become urine, which typically flows through the ureters to the bladder.

Extreme trauma may result in the loss of kidney function. This loss of function results in the retention of excess fluids within the kidneys and the build up of waste products, such as nitrogen. When the kidneys stop working over a period of hours, days, or weeks renal failure results. The most common causes of acute forms of renal failure include dehydration, direct trauma to the kidneys, decreased cardiac output, blood loss, and various medications; such as contrast agents used in X-ray tests, nonsteroidal anti-inflammatory drugs (NSAIDs), and antibiotics. During renal failure excess fluids are not removed by the kidneys and the body's normal chemical balance is upset as chemicals and electrolytes, such as sodium, potassium, and calcium, build up to abnormally high levels and become toxic to the body.

SUMMARY

Methods for treating a renal associated condition in a subject are provided. Aspects of the subject methods include paradoxically enhancing renal sympathetic bias in the subject to treat the renal associated condition. Also provided are compositions, kits and systems for practicing the subject methods.

BRIEF DESCRIPTIONS OF THE DRAWINGS

FIG. 1 shows an exemplary embodiment of an electric energy applying device operatively positioned in a subject's body in accordance with embodiments of the subject methods.

DESCRIPTION OF CERTAIN EMBODIMENTS

Methods for treating a renal associated condition in a subject are provided. Aspects of the subject methods include paradoxically enhancing renal sympathetic bias, i.e., enhancing renal sympathetic bias in a manner effective to cause the subject to mount a compensatory response to the enhanced renal sympathetic bias, to treat the renal associated condition. Also provided are compositions, kits and systems for practicing the subject methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods and Devices

Aspects of the invention include methods of treating a subject for a renal associated condition. In the subject methods, renal sympathetic bias is paradoxically enhanced. As such, renal sympathetic bias in the subject is enhance in a manner effective to cause the subject to mount a compensatory response effective to treat the renal associated condition. By "enhanced" is meant that the magnitude of sympathetic bias to the kidneys is increased. In other words, the renal sympathetic bias is exacerbated. In certain embodiments, the magnitude of enhancement is at least about two-fold, e.g., at least about 5-fold, or more.

By renal sympathetic bias is meant the sympathetic bias applied to one or both of the kidneys at a given time. By "bias" is meant that the particular "biased" component of the autonomic nervous system has a higher activity level than the other component. As such, sympathetic bias refers to a higher level of sympathetic activity than parasympathetic activity. The net result of the subject methods to treat a condition may be higher or greater sympathetic activity relative to parasympathetic activity in at least the area of the autonomic system targeted or rather in need of modulation, such as the kidneys.

In practicing the subject methods, the renal sympathetic bias is enhanced by applying an appropriate stimulus to the subject, where the stimulus is of a nature and magnitude sufficient to achieve the desired enhancement. In certain embodiments, the applied stimulus is one of short duration, where by short duration is meant that the applied stimulus lasts for less than about 1 week, e.g., less than about 3 days, e.g., less than about 1 day, e.g., less than about 12 hours, where the duration of the applied stimulus may be even shorter. Where the stimulus is an electrical stimulus, the duration refers to the total of electrical applications received by a subject over a given period.

Following renal sympathetic bias enhancement via an applied stimulus, as described above, the stimulus is removed, e.g., by cessation of application of electrical energy, and the subject is permitted to mount a compensatory response. In this following period, no additional stimulus is administered to the subject. The duration of this period between stimulus application, which may be referred to as a "holiday" period, may vary, but in certain embodiments is at least about 1 day, such as at least about 2 days, including at least about 5 days, at least about 10 days, at least about 15 days, or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the renal sympathetic bias enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in certain embodiments the stimulus may be an electrical stimulus. Accordingly, in certain embodiments, the enhancing is by electrical stimulation, e.g., by employing an implanted electrical energy application device.

A variety of different renal associated conditions are treatable by the subject methods. In certain embodiments, a renal condition such as chronic renal failure, acute renal failure, contrast nephropathy (e.g. iodine-based contrast nephropathy), cardiorenal syndrome, nephropathy and the like is the target renal associated condition. In certain embodiments, the renal condition is manifested by an increase in a hormone level, such as an increase in rennin, angiotensin, aldosterone, vasopressin, catecholamines, natriuretic peptides, and the like, and treatment involves the reduction of the indicative hormone level. Renal associated conditions are described in greater detail below.

As noted above, certain embodiments include employing electrical modulation, in a manner effective to cause the desired renal sympathetic bias enhancement according to the subject methods.

Any suitable area may be targeted for electrical modulation. Areas that may be targeted include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Specific areas of the nervous system which may be targeted in accordance with the subject invention include, but are not limited to, the renal nerve and plexus associated therewith. The autonomic nervous system forms a plexus on the external surface renal artery. Fibers contributing to the plexus arise from the celiac ganglion, the lowest splanchnic nerve, the aorticorenal ganglion and aortic plexus. The plexus is distributed with branches of the renal artery to vessels of the kidney, the glomeruli and tubules. The nerves from these sources, fifteen or twenty in number, have a few ganglia developed upon them. They accompany the branches of the renal artery into the kidney; some filaments are distributed to the spermatic plexus and, on the right side; to the inferior vena cava. Embodiments of the invention may include enhancing sympathetic bias of any of these nerves, where enhancing sympathetic bias of any of these nerves is considered to be enhancing sympathetic bias.

In certain embodiments, the parasympathetic/sympathetic activity ratio of kidneys is selectively increased. By selectively increased is meant that the activity ratio or bias of the kidneys is modulated to at least to a greater extent than other regions of the body, such that the ratio or bias is not systemically modulated. In certain of these embodiments, selectively increase the ratio or bias of the kidneys comprises exclusively modulating the ratio or bias of these organs, to the exclusion of other parts of the body. Selective modulation may be achieved using any convenient protocol, e.g., by selectively stimulating or pacing autonomic nerves innervating the kidneys, by selectively delivering pharmacological agents to the kidneys, etc. Localization may be with respect to a particular area, organ, e.g., kidney, or even to a particular nerve fiber. For example, localization may be with respect to innervations of one or more organs. Area(s) of the autonomic nervous system may include, but are not limited to, pre- and post ganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber. As such, representative embodiments of the invention are characterized in that the parasympathetic/sympathetic activity ratio of the kidney(s) is modulated, e.g. using any of a variety of methods described in this application.

A number of different devices may be employed in accordance with the subject invention. For example, device and systems for applying electrical energy to a subject and which may be adapted for use in the subject invention are described, e.g., in copending US patent published application nos.: 20040249416 and 20050021092, the disclosures which are herein incorporated by reference. Also of interest are the devices disclosed in U.S. Publication No. 20050234523, the disclosure of which is herein incorporated by reference. Such devices may be positioned directly on a targeted area, e.g., positioned below the skin of a subject directly on or adjacent a portion of the nervous-system (e.g., one or more nerve fibers) such as an implantable device, or may be an external device (i.e., some or all of the device may be external to the subject). In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed.

The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a-battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed).

A controller or programmer may also be coupled with an electric energy applying device. The programmer is typically one or more microprocessors under the control of a suitable software program. Other components of the programmer will be apparent to those of skill in the art, e.g., analog to digital converter, etc. The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power— either increasing or decreasing the power supplied depending on whether the magnet is brought in proximity or moved away from the power source.

FIG. 1 shows an exemplary embodiment of an electric energy applying device 100. Device 100 may be implanted in a suitable position of a subject's body 10. One or more leads 23 are shown positioned to stimulatory or inhibitory electrical energy. Device 100 includes energy source 14 which may take the form of a modified signal generator, Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by any convenient procedure.

Additional devices suitable for use in electrically enhancing renal sympathetic bias and methods for introducing the same to a patient are described in Published U.S. Application Nos. 20050234523 and 20030216792; the disclosures of which devices and procedures for temporary or permanent implantation thereof are incorporated herein by reference.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1-millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if a predetermined detection criteria is not detected the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

Utility

The subject methods find use in a variety of applications in which it is desired to treat a subject for a renal associated condition, e.g., a renal condition that may be influenced by an abnormality in the subject's autonomic nervous system (e.g., a sympathetic bias). In such methods, at least a portion of a subject's autonomic nervous system is modulated in a manner suitable to treat the subject for the condition, e.g., in a manner to paradoxically enhance renal sympathetic bias as described above.

The subject methods find use in the treatment of a variety of different renal associated conditions in which an abnormality in a subject's autonomic nervous system exists. By treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the renal condition being treated. As such, treatment also includes situations where the condition, or at least symptoms associated therewith, are completely inhibited, e.g. prevented from happening, or stopped, e.g. terminated, such that the subject no longer suffers from the renal associated condition, or at least the symptoms that characterize the condition. In certain embodiments, the condition being treated is a renal disease.

Abnormalities in a subject's autonomic nervous system may include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different renal associated conditions, including, but not limited to: acute and chronic renal failure, contrast nephropathy (e.g., iodine-based contrast nephropathy), cardiorenal syndrome (e.g., pulmonary renal syndrome), acidosis (e.g., renal tubular acidosis), nephropathy, and the like. The renal condition may be one that is induced by a trauma that results in the loss of kidney function or may be one that manifests as a result of an excessive retention of fluids and/or the retention of waste products, such as electrolytes e.g., nitrogen, sodium, potassium, calcium, etc. that build up to abnormally high levels within the kidneys and become toxic to the body. The renal condition may also be one that is induced by dehydration, decreased cardiac output, blood loss, and/or induced by the administration of various medications; such as contrast agents used in X-ray tests, nonsteroidal anti-inflammatory drugs (NSAIDs), and antibiotics. In certain embodiments, the renal condition is associated with or otherwise manifested by an increase in a hormone level, such as an increase in renin, angiotensin, aldosterone, vasopressin, catecholamines, natriutic peptides, and the like, and treatment involves at least the reduction of the indicative hormone level. Other renal associated conditions may also be treated in accordance with the subject invention. Embodiments of the subject invention include treating one or more conditions, sequentially or at the same time, in accordance with the subject invention.

In representative embodiments, the target renal condition that is treated is one that results from maladaptive activation of the renal trauma response, (e.g., where the maladaptive response is to conserve hemodynamic volume by reducing urine output), where such conditions include, but are not limited to, maladaptive response conditions instigated by heart failure, aging, atherosclerosis, renal artery stenosis, diabetes, contrast agent induced nephropathy, The target renal conditions which are treated in certain embodiments of the invention include those that are readily identified using any convenient diagnostic measure. There are several different diagnostic measures that can be evaluated to determine if a subject's kidneys are functioning within healthy parameters. For instance, several different blood or urine related factors (such as electrolytes) or fluid build up (edema) may be measured. For example, serum or urine creatinine and urea nitrogen levels may be measured. Creatinine is a waste product that comes from normal wear and tear on muscles of the body. Urea nitrogen is a waste product produced by metabolism of protein. As kidney disease progresses, the levels of creatinine and urea nitrogen in the blood increases. Although healthy levels of creatinine and urea nitrogen will vary, appropriate ranges can easily be determined by one of ordinary skill in the art. Levels of creatinine will normally be in the range of about 0.5 to about 1.5 mg/dl, from about 0.75 to about 1.25 mg/dl, or about 1 mg/dl. Levels of urea nitrogen will normally be in the range of about 0.5 to about 25 mg/dl, from about 10 to about 20 mg/dl, or about 15 mg/dl. Therefore higher levels of creatinine may be a sign that the kidneys are not working properly and an evaluation of sympathetic bias may be made. An ultrasound of the kidneys and/or a measurement of kidney size may also help determine whether kidneys are functioning properly.

Accordingly, in certain embodiments, the renal condition to be treated is manifested by or otherwise associated with an increase in a hormone level, such as an increase in rennin, angiotensin, aldosterone, vasopressin, catecholamines, natriutic peptides, and the like, and treatment involves the reduction of the indicative hormone level.

A variety of subjects are treatable according to the subject methods. In many embodiments the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

In certain embodiments, the subject methods are employed to treat non-renal conditions, e.g., conditions of other organs, where the non-renal conditions are impacted by the autonomic state of the kidney, where such conditions include, but are not limited to: cardio-renal conditions, hepatorenal conditions, pulmonary renal conditions, etc. In such applications, the renal sympathetic bias is paradoxically modulated in a manner effective to treat the non-renal condition. Representative conditions of interest include, but are not limited to: abnormalities in a subject's autonomic nervous system characterized by an abnormally high parasympathetic activity or abnormally low parasympathetic activity and/or an abnormally high sympathetic activity or abnormally low sympathetic activity.

Examples of conditions that may be treated with the methods of the subject invention include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma; CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant-related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyper-reninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary-pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

Additional conditions of interest that may be treated by embodiments of the subject methods include those described in U.S. patent application Ser. Nos. 10/661,368; 10/748,897; 10/748,976; 10/871,366; 10/846,486 10/917,270; 10/962,190 11/060,643 11/251,629; 11/238,108; 60/654,139 and 60/702,776; the disclosures of which are herein incorporated by reference.

Embodiments of the invention include methods of treating heart failure, renal failure and/or hypertension, and additional conditions as described in Published U.S. Application Nos. 20050234523 and 20030216792; the disclosures of which devices and procedures for temporary or permanent implantation thereof are incorporated herein by reference.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer electrical energy to a subject, e.g., may control the activation/termination of electrical energy including selecting suitable electrical parameters. Programming may be configured to, or otherwise be capable of, directing a microprocessor to activate, i.e., turn "on" and "off" an electric energy applying device for applying energy to a subject. For example, if so determined, the processor may direct the electric energy applying device to provide the appropriate energy to result in the desired action. Accordingly, a processor may select the appropriate parameters (e.g., frequency, amplitude, etc.) depending on what is required and direct an electric energy applying device to implement the parameters.

Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods; where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include an electric energy applying device, as described above. Devices for delivering, e.g., implanting, an electric energy applying device to a target site of a subject such as into the body cavity of a subject may also be included in the subject kits. For example, an endoscope, introducer needle, and the like may be provided.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example

Use of Paradoxical Renal Neurostimulation Device to Treat Hypertension

Double blinded randomized controlled studies were performed in a set of humans with essential hypertension to demonstrate that paradoxical renal neurostimulation lowered blood pressure. In all patients, hypertension was confirmed on at least three occasions in an outpatient setting after the patient had been sitting for at least 10 minutes. Blood pressure ranges recorded would indicate elevation of both systolic and diastolic components of the blood pressure. All medications were stopped for each individual for at least four weeks before the beginning of the study. All patients remained hospitalized throughout the study, where physical activity consisted of only daily walks. Diet was strictly monitored and standardized in terms of nutritional and caloric content. Implantation of the device was performed under regional anesthesia for all subjects in the treatment group; sham implantation was performed for all subjects in the control group. A 10 day steady state control period preceded the experimental period for all subjects. Throughout the experimental period, all patients in the treatment group underwent neurostimulation, frequency and intensity determined per standardized protocol based on response or lack thereof with respect to physiologic measurements. Blood pressure was measured in the nondominant arm at 8 am, noon, 4 pm, 8 pm, and 10 pm of each day with an automated oscillometric device in order to avoid observer bias. At each measurement session, after the patient was supine for 10 minutes, five measurements of systolic and diastolic pressure and heart rate were obtained and the average of the last four measurements calculated. The measurements were repeated with the patient in the upright position at each session. The measurements were averaged to yield values of daily systolic and diastolic blood pressure, and mean arterial pressures were calculated. Measurements continued for a recovery period of 15 days following completion of neurostimulation. All patients in the treatment group showed statistically meaningful decreases in systolic, diastolic, and mean arterial pressures as compared to the control group by the end of the treatment period, and these differences persisted throughout the recovery period.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a renal associated condition in a subject, said method comprising:
   paradoxically enhancing renal sympathetic bias non-chronically in said subject in a manner effective to cause the subject to mount a compensatory response to the enhanced renal sympathetic bias to treat said renal associated condition, wherein said enhancing comprises non-chronically applying an electrical stimulus to said subject.

2. The method according to claim 1, wherein said method comprises monitoring said subject.

3. The method according to claim 2, wherein said method comprises applying a first stimulus to said subject and monitoring said subject for a response thereto; and applying a second stimulus to said subject, wherein said second stimulus is determined based on said monitored response to said first stimulus.

4. The method of claim 1, wherein said renal associated condition comprises a member selected from the group consisting of acute renal failure, chronic renal failure, contrast nephropathy, cardiorenal syndrome, and hypertension.

5. The method of claim 4, wherein said renal condition is cardiorenal syndrome.

6. The method of claim 4, wherein said renal condition is contrast nephropathy.

7. The method of claim 6, wherein said contrast nephropathy is iodine-based contrast nephropathy.

8. An algorithm recorded on a computer-readable medium for administering a stimulus to said subject in accordance with method of claim 1.

9. A system comprising:
- an algorithm recorded on a computer-readable medium for administering a stimulus to a subject according to a method of claim 1; and
- a stimulus producing component, wherein said stimulus producing component is an electrical energy applying device.

10. A kit comprising:
- a stimulus producing component, wherein said stimulus producing component is an electrical energy applying device; and
- instructions for a stimulus to a subject according to the method of claim 1.

11. The method according to claim 1, wherein said renal sympathetic bias is enhanced at least about two-fold.

12. The method according to claim 1, wherein said stimulus is applied for less than one week.

13. The method according to claim 1, wherein applying said stimulus is followed by a holiday period in which no additional stimulus is administered to said subject, such that said subject is permitted to mount a compensatory response effective to treat said renal associated condition.

14. The method according to claim 13, wherein said holiday period is at least about 1 day.

15. The method according to claim 1, wherein said stimulus is applied in an irregularly irregular manner.

* * * * *

UNITED STATES PATENT AND TRADEMARK OFFICE
CERTIFICATE OF CORRECTION

| | | |
|---|---|---|
| PATENT NO. | : 8,571,650 B2 | Page 1 of 1 |
| APPLICATION NO. | : 11/713555 | |
| DATED | : October 29, 2013 | |
| INVENTOR(S) | : Yun | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1015 days.

Signed and Sealed this
Fourteenth Day of April, 2015

Michelle K. Lee
*Director of the United States Patent and Trademark Office*